United States Patent
Imagawa et al.

(10) Patent No.: US 11,377,433 B2
(45) Date of Patent: Jul. 5, 2022

(54) METHOD FOR PRODUCING POLYFUNCTIONAL SULFUR-CONTAINING EPOXY COMPOUND

(71) Applicant: MITSUBISHI GAS CHEMICAL COMPANY, INC., Tokyo (JP)

(72) Inventors: Yousuke Imagawa, Tokyo (JP); Hiroshi Horikoshi, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 17/042,505

(22) PCT Filed: Jun. 11, 2019

(86) PCT No.: PCT/JP2019/023009
§ 371 (c)(1),
(2) Date: Sep. 28, 2020

(87) PCT Pub. No.: WO2020/003999
PCT Pub. Date: Jan. 2, 2020

(65) Prior Publication Data
US 2021/0024478 A1  Jan. 28, 2021

(30) Foreign Application Priority Data
Jun. 29, 2018 (JP) .............................. JP2018-124395

(51) Int. Cl.
*C07D 301/28* (2006.01)
*C07D 303/34* (2006.01)

(52) U.S. Cl.
CPC ......... *C07D 301/28* (2013.01); *C07D 303/34* (2013.01)

(58) Field of Classification Search
None
See application file for complete search history.

(56) References Cited

U.S. PATENT DOCUMENTS

| | | | |
|---|---|---|---|
| 5,807,975 A | 9/1998 | Amagai et al. | |
| 5,834,621 A | 11/1998 | Yamamoto et al. | |
| 5,945,504 A | 8/1999 | Amagi et al. | |
| 2014/0371475 A1 | 12/2014 | Aoki et al. | |
| 2017/0247351 A1 | 8/2017 | Nishimori et al. | |

FOREIGN PATENT DOCUMENTS

| | | | |
|---|---|---|---|
| CN | 109666093 | * | 4/2019 |
| JP | 9-71580 A | | 3/1997 |
| JP | 9-110979 A | | 4/1997 |
| JP | 9-255781 A | | 9/1997 |
| JP | 10-130250 A | | 5/1998 |
| JP | 2000-143651 A | | 5/2000 |
| JP | 2003-48883 A | | 2/2003 |
| JP | 2013087085 | * | 5/2013 |
| WO | 2013/157490 A1 | | 10/2013 |
| WO | 2016/158157 A1 | | 10/2016 |

OTHER PUBLICATIONS

CAPLUS printout of "Chlebicki, J. The oxidation of 1-chloro-3-alkylthio-2-propanols and 1-alkylthio-2,3-epoxypropanes to sulfoxide and sulfones. Polish Journal of APplied CHemistry, 2004, 48, 23-31."*
Kuo et al., Generation of Gold Thread from Au(III) and Triethylamine. Langmuir, 2006, 22, 7902-7906.*
CAPLUS printout of Foreign Patent No. CN109666093, published on Apr. 23, 2019.*
Machine-generated English translation of Foreign Patent No. CN 109666093, published on Apr. 23, 2019.*
Stefaniak et al., Application of HPLC for the screening of separation of new macrocyclic systems. Phosphorus, Sulfur, and Silicon and the Related Elements, 2017, 192-245-248 (published online on Nov. 10, 2016).*
CAPLUS printout of "Stefaniak et al., Application of HPLC for the screening of separation of new macrocyclic systems. Phosphorus, Sulfur, and Silicon and the Related Elements, 2017, 192-245-248 (published online on Nov. 10, 2016)."*
Feng et al., Effect of Reducing Agent on the Chemical Reduction of Graphene Oxides. Journal of Nanoscience and Nanotechnology, 2013, 13, 937-941.*
CAPLUS printout of Foreign Patent Application Publication No. JP2013087085, published on May 13, 2013.*
Machined-generated English translation of Foreign Patent No. JP2013087085, published on May 13, 2013.*
International Search Report issued in International Patent Application No. PCT/JP2019/023009, dated Sep. 3, 2019, along with an English translation thereof.
EESR issued in European Patent Application No. 19825577.0, dated Jun. 7, 2021.

* cited by examiner

*Primary Examiner* — Po-Chih Chen
(74) *Attorney, Agent, or Firm* — Greenblum & Bernstein, P.L.C.

(57) ABSTRACT

The present invention makes it possible to provide a method for producing a polyfunctional sulfur-containing epoxy compound, the method being characterized in that a polyfunctional thiol is reacted with an epihalohydrin in the presence of a reducing agent to form a polyfunctional sulfur-containing halohydrin, which is then reacted with a basic compound. The reducing agent is preferably at least one selected from the group consisting of sodium borohydride, lithium borohydride, lithium aluminum hydride, diisobutylaluminum hydride, and hydrazine.

7 Claims, No Drawings

METHOD FOR PRODUCING POLYFUNCTIONAL SULFUR-CONTAINING EPOXY COMPOUND

TECHNICAL FIELD

The present invention relates to a polyfunctional sulfur-containing epoxy compound and a method for producing the same. The present invention particularly relates to a polyfunctional sulfur-containing epoxy compound serving as a raw material of a polyfunctional episulfide compound that is suitably used for an optical material for a plastic lens, a prism, an optical fiber, an information recording substrate, a filter or the like, in particular for a plastic lens, and a method for producing the same.

BACKGROUND ART

Plastic materials are lightweight, highly tough and easy to be dyed, and therefore are widely used recently for various types of optical materials, particularly eyeglass lenses. Optical materials, particularly eyeglass lenses, are specifically required to have, as physical properties, low specific gravity, high transparency and low yellowness, high heat resistance, high strength and the like, and as optical properties, high refractive index and high Abbe number. A high refractive index allows a lens to be thinner, and a high Abbe number reduces the chromatic aberration of a lens. However, as the refractive index is increased, the Abbe number tends to be decreased. Therefore, it has been studied to improve both of the refractive index and the Abbe number. Among methods which have been proposed, the most representative methods are those using a polyfunctional episulfide compound described in Patent Documents 1-3.

These polyfunctional episulfide compounds are obtained by producing a sulfur-containing epoxy compound in which a sulfur atom at the epithio moiety is an oxygen atom and then thialating the compound. As methods for producing a polyfunctional sulfur-containing epoxy compound, the production methods described in Patent Documents 4-6 have been proposed, and the improvement of the yield, the improvement of transparency of a resin obtained by curing a polyfunctional episulfide compound obtained by thialation, and a production method in which no scum-like insoluble matter is generated are disclosed.

However, by these production methods, the color tone, in particular, yellowing of the polyfunctional sulfur-containing epoxy compound is not sufficiently improved, and the color tone of an episulfide compound obtained by subsequent thialation is also affected thereby. Accordingly, it has been desired to develop a method for producing a polyfunctional sulfur-containing epoxy compound, wherein the color tone is satisfactory, and in particular, yellowing is suppressed.

PRIOR ART DOCUMENTS

Patent Documents

Patent Document 1: Japanese Laid-Open Patent Publication No. H09-71580
Patent Document 2: Japanese Laid-Open Patent Publication No. H09-110979
Patent Document 3: Japanese Laid-Open Patent Publication No. H09-255781
Patent Document 4: Japanese Laid-Open Patent Publication No. 2000-143651
Patent Document 5: Japanese Laid-Open Patent Publication No. 2003-48883
Patent Document 6: International Publication WO2013/157490 pamphlet

SUMMARY OF THE INVENTION

Problems to be Solved by the Invention

The problem to be solved by the present invention is to provide a method for producing a polyfunctional sulfur-containing epoxy compound, wherein the color tone is satisfactory, and in particular, yellowing is suppressed.

Means for Solving the Problems

The present inventors diligently made researches in consideration of the above-described circumstances and found that a polyfunctional sulfur-containing epoxy compound, wherein the color tone is satisfactory, and in particular, yellowing is suppressed, is obtained by reacting a polyfunctional thiol with an epihalohydrin in the presence of a reducing agent and then reacting the obtained material with a basic compound. Specifically, the present invention is as described below.

<1> A method for producing a polyfunctional sulfur-containing epoxy compound, wherein a polyfunctional thiol is reacted with an epihalohydrin in the presence of a reducing agent to form a polyfunctional sulfur-containing halohydrin, which is then reacted with a basic compound.
<2> The method according to item <1>, wherein the polyfunctional thiol is at least one selected from the group consisting of bis(2-mercaptoethyl)sulfide, 4-mercaptomethyl-1,8-dimercapto-3,6-dithiaoctane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,2,6,7-tetramercapto-4-thiaheptane and pentaerythrithiol.
<3> The method according to item <1> or <2>, wherein the reducing agent is at least one selected from the group consisting of sodium borohydride, lithium borohydride, lithium aluminum hydride, diisobutylaluminum hydride and hydrazine.
<4> The method according to any one of items <1> to <3>, wherein the basic compound is at least one selected from the group consisting of sodium hydroxide, potassium hydroxide and calcium hydroxide.
<5> The method according to any one of items <1> to <4>, wherein the reaction temperature is −5° C. to 30° C.

Advantageous Effect of the Invention

According to the production method of the present invention, it is possible to produce a polyfunctional sulfur-containing epoxy compound, wherein the color tone is satisfactory, and in particular, yellowing is suppressed, which was not successfully obtained by conventional production methods. Since yellowing is suppressed by the production method of the present invention, transparency of optical materials is improved, and it is very meaningful.

EMBODIMENTS FOR CARRYING OUT THE INVENTION

The present invention is characterized in that a polyfunctional thiol is reacted with an epihalohydrin in the presence of a reducing agent to form a polyfunctional sulfur-containing halohydrin, which is then reacted with a basic compound.

The polyfunctional thiol compound to be used in the present invention is a compound having at least two thiol groups and includes every polyfunctional thiol compound. Specific examples thereof include methanedithiol, methanetrithiol, 1,2-dimercaptoethane, 1,2-dimercaptopropane, 1,3-dimercaptopropane, 2,2-dimercaptopropane, 1,4-dimercaptobutane, 1,6-dimercaptohexane, bis(2-mercaptoethyl)ether, bis(2-mercaptoethyl)sulfide, 1,2-bis(2-mercaptoethyloxy)ethane, 1,2-bis(2-mercaptoethylthio)ethane, 2,3-dimercapto-1-propanol, 1,3-dimercapto-2-propanol, 1,2,3-trimercaptopropane, 2-mercaptomethyl-1,3-dimercaptopropane, 2-mercaptomethyl-1,4-dimercaptobutane, 2-(2-mercaptoethylthio)-1,3-dimercaptopropane, 4-mercaptomethyl-1,8-dimercapto-3,6-dithiaoctane, 2,4-dimercaptomethyl-1,5-dimercapto-3-thiapentane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1-tris(mercaptomethyl)propane, tetrakis(mercaptomethyl)methane, ethyleneglycol bis(2-mercapto acetate), ethyleneglycol bis(3-mercaptopropionate), diethyleneglycol bis(2-mercaptoacetate), diethyleneglycol bis(3-mercaptopropionate), 1,4-butanediol bis(2-mercaptoacetate), 1,4-butanediol bis(3-mercaptopropionate), trimethylolpropane tris(thioglycolate), trimethylolpropane tris(mercapto propionate), pentaerythritol tetrakis-thioglycolate, pentaerythritol tetrakis-mercaptopropionate, 1,2-dimercaptocyclohexane, 1,3-dimercaptocyclohexane, 1,4-dimercaptocyclohexane, 1,3-bis(mercaptomethyl)cyclohexane, 1,4-bis(mercaptomethyl)cyclohexane, 2,5-dimercaptomethyl-1,4-dithiane, 2,5-dimercaptomethyl-1,4-dithiane, 2,5-bis(2-mercaptoethylthiomethyl)-1,4-dithiane, 2,5-dimercaptomethyl-1-thiane, 2,5-dimercaptoethyl-1-thiane, 2,5-dimercaptomethylthiophene, 1,2-dimercaptobenzene, 1,3-dimercaptobenzene, 1,4-dimercaptobenzene, 1,3-bis(mercaptomethyl)benzene, 1,4-bis(mercaptomethyl)benzene, 2,2'-dimercaptobiphenyl, 4,4'-dimercaptobiphenyl, bis(4-mercaptophenyl)methane, 2,2-bis(4-mercaptophenyl)propane, bis(4-mercaptophenyl)ether, bis(4-mercaptophenyl)sulfide, bis(4-mercaptophenyl)sulfone, bis(4-mercaptomethylphenyl)methane, 2,2-bis(4-mercaptomethylphenyl)propane, bis(4-mercaptomethylphenyl)ether, bis(4-mercaptomethylphenyl)sulfide, 2,5-dimercapto-1,3,4-thiadiazole, 3,4-thiophenedithiol, 1,1,3,3-tetrakis(mercaptomethylthio)propane, 1,2,6,7-tetramercapto-4-thiaheptane and pentaerythrithiol.

Among them, preferred specific examples are bis(2-mercaptoethyl)sulfide, 4-mercaptomethyl-1,8-dimercapto-3,6-dithiaoctane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,2,6,7-tetramercapto-4-thiaheptane and pentaerythrithiol, and pentaerythrithiol is most preferred.

These compounds may be used solely, or two or more of them may be used in combination.

The reducing agent to be used in the present invention includes every reducing agent. Specific examples thereof include sodium borohydride, lithium borohydride, sodium cyanoborohydride, lithium aluminum hydride, diisobutylaluminum hydride, hydrazine, zinc, tin, iron, platinum, palladium and nickel. Among them, preferred compounds are sodium borohydride, lithium borohydride, lithium aluminum hydride, diisobutylaluminum hydride and hydrazine, and sodium borohydride is most preferred.

The amount of the reducing agent to be added is not particularly limited as long as it is for promoting a reaction, but is preferably 0.0001 to 5.0 mol, more preferably 0.01 to 1.0 mol, and most preferably 0.05 to 0.5 mol relative to 1 mol of the thiol group (SH group) of the polyfunctional thiol compound. When the amount is less than 0.0001 mol, it is undesirable because yellowing cannot be sufficiently suppressed, and when the amount is more than 5.0 mol, such an excess amount is undesirable from the economical viewpoint.

As the reducing agent, the above-described compounds may be used solely, or two or more of them may be used in combination.

Hereinafter, synthesis of a polyfunctional sulfur-containing halohydrin compound will be described.

The polyfunctional sulfur-containing halohydrin compound is obtained by reacting the polyfunctional thiol compound with an epihalohydrin in the presence of the reducing agent. Specific examples of the epihalohydrin include epichlorohydrin and epibromohydrin, and preferred is epichlorohydrin.

When reacting the polyfunctional thiol compound with the epihalohydrin, a catalyst is preferably used. Examples of the catalyst include inorganic acids, organic acids, Lewis acids, silicic acid, boric acid, quaternary ammonium salts, inorganic bases and organic bases. Among them, organic acids, quaternary ammonium salts and inorganic bases are preferred, and quaternary ammonium salts and inorganic bases are more preferred. Specific examples thereof include tetramethylammonium chloride, tetramethylammonium bromide, tetramethylammonium acetate, tetraethylammonium chloride, tetraethylammonium bromide, tetraethylammonium acetate, tetrabutylammonium chloride, tetrabutylammonium bromide, tetrabutylammonium acetate, tetrahexylammonium chloride, tetrahexylammonium bromide, tetrahexylammonium acetate, tetraoctylammonium chloride, tetraoctylammonium bromide, tetraoctylammonium acetate, sodium hydroxide, potassium hydroxide, magnesium hydroxide and calcium hydroxide. Among them, sodium hydroxide, potassium hydroxide and calcium hydroxide are preferred.

The amount of the catalyst to be added is not particularly limited as long as it is for promoting a reaction, but is preferably 0.00001 to 0.5 mol, and more preferably 0.001 to 0.1 mol per 1 mol of the epihalohydrin. When the amount is less than 0.00001 mol, the reaction does not proceed or is too slow, and it is undesirable. When the amount is more than 0.5 mol, the reaction proceeds excessively and is difficult to be controlled, and it is undesirable.

The ratio between the epihalohydrin and the polyfunctional thiol compound is not particularly limited as long as the reaction proceeds, but the molar ratio of epichlorohydrin to the thiol group (SH group) of the polyfunctional thiol compound is preferably 0.3 to 4, more preferably 0.4 to 3, and even more preferably 0.5 to 2. When the molar ratio is less than 0.3 or more than 4, the amount of unreacted raw materials increases, and it is undesirable from the economical viewpoint.

The reaction temperature is not particularly limited as long as it is for promoting a reaction, but is preferably −10° C. to 100° C., more preferably −5° C. to 80° C., even more preferably −5° C. to 60° C., and most preferably −5° C. to 30° C. The reaction time is not particularly limited, but is usually 10 minutes to 20 hours. When the reaction temperature is lower than −10° C., the reaction does not proceed or is too slow, and it is undesirable. When the reaction temperature is higher than 100° C., oligomerization occurs, resulting in a high molecular weight, and it is undesirable.

When obtaining the polyfunctional sulfur-containing halohydrin compound, it is preferred to use an organic solvent. According to a more preferred reaction technique, the epihalohydrin is added dropwise to a mixed solvent of the organic solvent and a solution of the basic compound to cause a reaction to obtain the polyfunctional sulfur-containing halohydrin compound.

Any organic solvent may be used without particular limitation, but preferably, alcohols, ethers, ketones, aliphatic hydrocarbons, aromatic hydrocarbons and halogenated hydrocarbons are used. These substances may be used solely, or two or more of them may be used in combination. Specific examples of the alcohols include methanol, ethanol, propanol and isopropanol. Specific examples of the ethers include diethyl ether, tetrahydrofuran and dioxane. Specific examples of the ketones include methyl cellosolve, ethyl cellosolve, butyl cellosolve, methyl ethyl ketone and acetone. Specific examples of the aliphatic hydrocarbons include hexane, heptane and octane. Specific examples of the aromatic hydrocarbons include benzene, toluene and xylene. Specific examples of the halogenated hydrocarbons include dichloroethane, chloroform and chlorobenzene. More preferred are alcohols, aliphatic hydrocarbons, aromatic hydrocarbons and halogenated hydrocarbons, and specific examples thereof include methanol, propanol, isopropanol, hexane, heptane, benzene, toluene and chloroform. Among them, preferred are alcohols, aromatic hydrocarbons and halogenated hydrocarbons, and specific examples thereof include methanol, propanol, isopropanol, benzene, toluene and chloroform. Even more preferred are alcohols and aromatic hydrocarbons, and specific examples thereof include methanol, isopropanol, benzene and toluene. Most preferred are methanol and toluene.

The amount of the organic solvent is not particularly limited, but is usually 5 to 5000% by weight, preferably 50 to 3000% by weight, and more preferably 100 to 1000% by weight per 100% by weight of the polyfunctional sulfur-containing halohydrin compound.

The reaction may be a two-phase system of the organic solvent and water. In this case, a phase transfer catalyst can be used. The phase transfer catalyst is a catalyst soluble in both the organic solvent and water, and as the phase transfer catalyst, a generally known material can be used without limitation.

Specific examples thereof include quaternary ammonium salts and quaternary phosphonium salts.

Examples of the quaternary ammonium salts include tetramethylammonium hydroxide, tetraethylammonium hydroxide, tetrabutylammonium hydroxide, trimethylbenzylammonium hydroxide, tetramethylammonium bromide, tetraethylammonium bromide, tetrabutylammonium bromide, trimethylbenzylammonium bromide, trimethylphenylammonium bromide, tetramethylammonium chloride, tetraethylammonium chloride, tetrabutylammonium chloride, trimethylbenzylammomium chloride, trimethylphenylammonium chloride, trioctylmethylammonium chloride, tributylbenzylammonium chloride, N-laurylpyridinium chloride, N-benzylpicolinium chloride, N-lauryl-4-picolinium chloride, N-laurylpicolinium chloride, tricaprylmethylammonium chloride, tetramethylammonium iodide, tetra-n-butylammonium iodide and tetrabutylammoniumhydrogen sulfate.

Examples of the quaternary phosphonium salts include tetraethylphosphonium chloride, tetraethylphosphonium bromide, tetraethylphosphonium iodide, tetrabutylphosphonium bromide, triphenylbenzylphosphonium bromide and tetraphenylphosphonium bromide.

The amount of the phase transfer catalyst to be used is not particularly limited, but it is preferably 0.01 to 30 mol %, and from the viewpoint of the reaction yield, the amount is more preferably 0.1 to 20 mol % relative to the polyfunctional thiol compound.

When reacting the polyfunctional thiol compound with the epihalohydrin, it is preferred to add the epihalohydrin dropwisely. When adding the epihalohydrin dropwisely to be reacted, the method for adding the epihalohydrin dropwisely is not particularly limited. The epihalohydrin may be directly added dropwisely, or may be dissolved in a solvent and then added dropwisely. Preferred is a method of directly adding the epihalohydrin dropwisely.

After the epihalohydrin is reacted, an acid may be added. Any acid can be used as long as it is acidic, but industrially inexpensive sulfuric acid, hydrochloric acid, nitric acid, phosphoric acid and aqueous solutions thereof can be suitably used, and sulfuric acid is preferred because it does not have volatility and is highly stable.

The amount of the acid to be added is not particularly limited, but it is preferably 0.1 to 5.0 equivalents, and more preferably 0.5 to 3.0 equivalents relative to the amount of the reducing agent (preferably sodium borohydride) to be added.

When adding the acid, it is preferred to add the acid dropwisely from the viewpoint of suppressing foaming. When adding the acid dropwisely to be reacted, the method for adding the acid dropwisely is not particularly limited.

The polyfunctional sulfur-containing halohydrin compound obtained in this way is reacted with a basic compound to obtain a polyfunctional sulfur-containing epoxy compound.

The basic compound to be used in the present invention is not particularly limited and any basic compound may be used, but it is preferably an alkali metal or alkaline earth metal salt. Preferred specific examples thereof include sodium carbonate, potassium carbonate, magnesium carbonate, calcium carbonate, sodium hydrogencarbonate, potassium hydrogencarbonate, sodium hydroxide, potassium hydroxide, magnesium hydroxide and calcium hydroxide. Among them, preferred are sodium hydroxide, potassium hydroxide, magnesium hydroxide and calcium hydroxide, and more preferred are sodium hydroxide and potassium hydroxide.

These materials may be used solely, or two or more of them may be used in combination.

The basic compound is used preferably in an amount of 0.5 to 10 equivalents per 1 equivalent of the polyfunctional sulfur-containing halohydrin compound. The amount is more preferably 0.7 to 5 equivalents, and particularly preferably 0.8 to 2 equivalents. When the amount is less than 0.5 equivalent or more than 10 equivalents, the amount of unreacted raw materials increases, and it is undesirable from the economical viewpoint.

The above-described basic compound is usually used in the form of an aqueous solution, alcohol solution or mixed solution of water and alcohol. The amount of the solvent is not particularly limited as long as the basic compound dissolves therein.

When reacting the polyfunctional sulfur-containing halohydrin compound with the basic compound, the polyfunctional halohydrin compound may be isolated but does not have to be isolated after synthesis thereof. Preferred is a method of reacting the polyfunctional sulfur-containing halohydrin compound with the basic compound without isolation after synthesis.

In the case where the polyfunctional sulfur-containing halohydrin compound is used for the next reaction without isolation after synthesis, the raw materials, solvent, catalyst, etc. used for synthesis of the polyfunctional sulfur-containing halohydrin compound may remain.

When reacting the polyfunctional sulfur-containing halohydrin compound with the basic compound, it is preferred to add the basic compound dropwisely. When adding the basic compound dropwisely to be reacted, the method for adding the basic compound dropwisely is not particularly limited. The basic compound may be directly added dropwisely, or may be dissolved in a solvent and then added dropwisely. Preferred is a method of dissolving the basic compound in a solvent and then adding it dropwisely.

In the case where the basic compound is dissolved in a solvent and then added dropwisely, the solvent to be used is not particularly limited, but preferably, water, alcohols, ethers, ketones, aliphatic hydrocarbons, aromatic hydrocarbons and halogenated hydrocarbons are used. These substances may be used solely, or two or more of them may be used in combination. Specific examples of the alcohols include methanol, ethanol, propanol and isopropanol. Specific examples of the ethers include diethyl ether, tetrahydrofuran and dioxane. Specific examples of the ketones include methyl cellosolve, ethyl cellosolve, butyl cellosolve, methyl ethyl ketone and acetone. Specific examples of the aliphatic hydrocarbons include hexane, heptane and octane. Specific examples of the aromatic hydrocarbons include benzene, toluene and xylene. Specific examples of the halogenated hydrocarbons include dichloroethane, chloroform and chlorobenzene. More preferred are water and alcohols, and specific examples thereof include water, methanol, propanol and isopropanol. Among them, preferred are water and methanol. The amount of the solvent is not particularly limited, but it is usually 5 to 1000% by weight, preferably 50 to 500% by weight, and more preferably 100 to 300% by weight per 100% by weight of the polyfunctional sulfur-containing halohydrin compound.

The reaction temperature for reacting the polyfunctional sulfur-containing halohydrin compound with the basic compound is not particularly limited as long as it is for promoting the reaction, but it is preferably −10° C. to 80° C., more preferably −5° C. to 50° C., and even more preferably −5° C. to 30° C. The reaction time is not particularly limited, but is usually 24 hours or less. When the reaction temperature is lower than −10° C., the reaction does not proceed or is too slow, and it is undesirable. When the reaction temperature is higher than 80° C., oligomerization occurs, resulting in a high molecular weight, and it is undesirable.

After the reaction is completed, an organic layer may be directly separated, or an organic solvent may be additionally fed thereto to perform extraction. The obtained organic layer is washed with water to remove the basic compound. After that, the organic solvent is distilled away, thereby obtaining the polyfunctional sulfur-containing epoxy compound.

EXAMPLES

Hereinafter, the present invention will be specifically described based on working examples, but the present invention is not limited thereto.

<Purity>: The epoxy compound produced was diluted to 0.1% with acetonitrile and analyzed by means of HPLC. LC-LOAD manufactured by Shimadzu Corporation was used as a liquid delivery pump, VP-ODS was used as a column, and RID-10A was used as a detector. While keeping the temperature at 40° C. using a column oven, a solution in which acetonitrile:water=1:1 was flowed at a rate of 0.7 mL/min to carry out the analysis.

<APHA value>: The measurement was carried out using a Hazen meter HM-IV (manufactured by X DENSHI SEKKEI, K.K.).

<Color tone evaluation>: The case where the APHA value was 0 or more but less than 50 was rated as A, the case where the APHA value was 50 or more but less than 100 was rated as B, and the case where the APHA value was 100 or more was rated as C. A and B are regarded as acceptable.

Example 1

In a four-neck flask equipped with a thermometer and a dropping funnel, 10.0 g (49.9 mmol) of pentaerythrithiol synthesized based on Japanese Patent No. 3222940 was put, and a reaction container was subjected to substitution with nitrogen. After that, a solution obtained by dissolving 0.42 g of 48% aqueous solution of sodium hydroxide in 39.6 g of methanol and 86.7 g of toluene were additionally put in the reaction container, and the mixture was cooled to 5° C. while stirring. Subsequently, as a reducing agent, 0.94 g (25.0 mmol) of sodium borohydride was put therein, and the mixture was stirred for 2 hours. Further, 20.3 g (219.6 mmol) of epichlorohydrin was added thereto dropwisely with the solution temperature being kept at 5 to 15° C. while stirring, thereby obtaining tetrakis(3-chloro-2-hydroxypropylthiomethyl)methane.

Next, a solution obtained by dissolving 18.3 g of 48% aqueous solution of sodium hydroxide in 15.8 g of methanol was added thereto dropwisely with the solution temperature being kept at 5 to 15° C. After it was completed, the solution temperature was kept at 15° C. and the mixture was matured for 20 hours. An organic layer was washed with 100 g of water 3 times, and then the solvent was distilled away, thereby obtaining 20.9 g (total yield: 99%) of tetrakis(β-epoxypropylthiomethyl)methane. The purity of the obtained tetrakis(β-epoxypropylthiomethyl)methane was 100%, and the APHA value was 38.

Examples 2-4

The operation was carried out in a manner similar to that in Example 1, except that the amount of the reducing agent was as described in Table 1.

Example 5

In a four-neck flask equipped with a thermometer and a dropping funnel, 10.0 g (49.9 mmol) of pentaerythrithiol synthesized based on Japanese Patent No. 3222940 was put, and a reaction container was subjected to substitution with nitrogen. After that, 86.7 g of toluene was additionally put in the reaction container, and the mixture was cooled to 5° C. while stirring. Subsequently, a solution obtained by dissolving 0.42 g of 48% aqueous solution of sodium hydroxide and 0.94 g (25.0 mmol) of sodium borohydride as a reducing agent in 67 g of water was put therein, and the mixture was stirred. After that, 1.61 g (5.0 mmol) of tetrabutylammonium bromide was added thereto, and the mixture was stirred for 4 hours. Further, 20.3 g (219.6 mmol) of epichlorohydrin was added thereto dropwisely with the solution temperature being kept at 5 to 15° C. while stirring, thereby obtaining tetrakis(3-chloro-2-hydroxypropylthiomethyl)methane.

Next, 14.7 g of 20% aqueous solution of sulfuric acid was added thereto dropwisely with careful attention to foaming, and the mixture was stirred for 30 minutes. Further, a solution obtained by dissolving 31.6 g of 48% aqueous solution of sodium hydroxide in 15.8 g of water was added thereto dropwisely with the solution temperature being kept at 5 to 15° C. After it was completed, the solution temperature was kept at 15° C. and the mixture was matured for 20 hours. An organic layer was washed with 100 g of water 3 times, and then the solvent was distilled away, thereby obtaining 20.9 g (total yield: 99%) of tetrakis(β-epoxypropylthiomethyl)methane. The purity of the obtained tetrakis(β-epoxypropylthiomethyl)methane was 100%, and the APHA value was 36.

Examples 6-8

The operation was carried out in a manner similar to that in Example 1, except that the compound shown in Table 1 was used as the thiol.

Example 9

The operation was carried out in a manner similar to that in Example 1, except that the compound shown in Table 1 was used as the reducing agent.

Comparative Example 1

20.8 g (total yield: 99%) of tetrakis(β-epoxypropylthiomethyl)methane was obtained in a manner similar to that in Example 1, except that no reducing agent was used. The purity of the obtained tetrakis(β-epoxypropylthiomethyl) methane was 99%, and the APHA value was 140.

In Comparative Example 1, the color tone was deteriorated because no reducing agent was used.

The invention claimed is:

1. A method for producing a sulfur-containing epoxy compound, which comprises:
reacting a polyfunctional thiol compound having at least two thiol groups with an epihalohydrin in the presence of a reducing agent to form a sulfur-containing halohydrin, and then
reacting the sulfur-containing halohydrin with a basic compound to form the sulfur-containing epoxy compound;
wherein the polyfunctional thiol compound is at least one selected from the group consisting of bis(2-mercaptoethyl)sulfide, 4-mercaptomethyl-1,8-dimercapto-3,6-dithiaoctane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,2,6,7-tetramercapto-4-thiaheptane and pentaerythrithiol; and
wherein the reducing agent is at least one selected from the group consisting of sodium borohydride, lithium borohydride, lithium aluminum hydride, diisobutylaluminum hydride, and hydrazine.

2. A method for producing a sulfur-containing epoxy compound, which comprises:
reacting a polyfunctional thiol compound having at least two thiol groups with an epihalohydrin in the presence of a reducing agent to form a sulfur-containing halohydrin, and then
reacting the sulfur-containing halohydrin with a basic compound to form the sulfur-containing epoxy compound;
wherein the reducing agent is at least one selected from the group consisting of sodium borohydride, lithium borohydride, lithium aluminum hydride, diisobutylaluminum hydride and hydrazine.

3. The method according to claim 1, wherein the basic compound is at least one selected from the group consisting of sodium hydroxide, potassium hydroxide and calcium hydroxide.

TABLE 1

| Examples | Thiol | Reducing agent | Reducing agent/thiol group [mol/mol] | Purity [%] | APHA value | Color tone evaluation |
|---|---|---|---|---|---|---|
| Example 1 | Pentaerythrithiol | Sodium borohydride | 0.13 | 100 | 38 | A |
| Example 2 | Pentaerythrithiol | Sodium borohydride | 0.050 | 100 | 49 | A |
| Example 3 | Pentaerythrithiol | Sodium borohydride | 0.025 | 100 | 60 | B |
| Example 4 | Pentaerythrithiol | Sodium borohydride | 0.012 | 100 | 98 | B |
| Example 5 | Pentaerythrithiol | Sodium borohydride | 0.13 | 100 | 36 | A |
| Example 6 | Bis(2-mercaptoethyl)sulfide | Sodium borohydride | 0.13 | 100 | 5 | A |
| Example 7 | 4-mercaptomethyl-1,8-dimercapto-3,6-dithiaoctane | Sodium borohydride | 0.13 | 100 | 5 | A |
| Example 8 | 1,2,6,7-tetramercapto-4-thiaheptane | Sodium borohydride | 0.13 | 100 | 5 | A |
| Example 9 | Pentaerythrithiol | Lithium borohydride | 0.13 | 100 | 35 | A |
| Comparative Example 1 | Pentaerythrithiol | Not used | — | 99 | 140 | C |

4. The method according to claim 2, wherein the basic compound is at least one selected from the group consisting of sodium hydroxide, potassium hydroxide and calcium hydroxide.

5. The method according to claim 1, wherein reaction temperature is from −5° C. to 30° C.

6. The method according to claim 2, wherein reaction temperature is from −5° C. to 30° C.

7. The method according to claim 2, wherein the polyfunctional thiol compound is at least one selected from the group consisting of methanedithiol, methanetrithiol, 1,2-dimercaptoethane, 1,2-dimercaptopropane, 1,3-dimercaptopropane, 2,2-dimercaptopropane, 1,4-dimercaptobutane, 1,6-dimercaptohexane, bis(2-mercaptoethyl)ether, bis(2-mercaptoethyl)sulfide, 1,2-bis(2-mercaptoethyloxy)ethane, 1,2-bis(2-mercaptoethylthio)ethane, 2,3-dimercapto-1-propanol, 1,3-dimercapto-2-propanol, 1,2,3-trimercaptopropane, 2-mercaptomethyl-1,3-dimercaptopropane, 2-mercaptomethyl-1,4-dimercaptobutane, 2-(2-mercaptoethylthio)-1,3-dimercaptopropane, 4-mercaptomethyl-1,8-dimercapto-3,6-dithiaoctane, 2,4-dimercaptomethyl-1,5-dimercapto-3-thiapentane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1-tris(mercaptomethyl)propane, tetrakis(mercaptomethyl)methane, ethyleneglycol bis(2-mercaptoacetate), ethyleneglycol bis(3-mercaptopropionate), diethyleneglycol bis(2-mercaptoacetate), diethyleneglycol bis(3-mercaptopropionate), 1,4-butanediol bis(2-mercaptoacetate), 1,4-butanediol bis(3-mercaptopropionate), trimethylolpropane tris(thioglycolate), trimethylolpropane tris(mercaptopropionate), pentaerythritol tetrakis-thioglycolate, pentaerythritol tetrakis-mercaptopropionate, 1,2-dimercaptocyclohexane, 1,3-dimercaptocyclohexane, 1,4-dimercaptocyclohexane, 1,3-bis(mercaptomethyl)cyclohexane, 1,4-bis(mercaptomethyl)cyclohexane, 2,5-dimercaptomethyl-1,4-dithiane, 2,5-dimercaptomethyl-1,4-dithiane, 2,5-bis(2-mercaptoethylthiomethyl)-1,4-dithiane, 2,5-dimercaptomethyl-1-thiane, 2,5-dimercaptoethyl-1-thiane, 2,5-dimercaptomethylthiophene, 1,2-dimercaptobenzene, 1,3-dimercaptobenzene, 1,4-dimercaptobenzene, 1,3-bis(mercaptomethyl)benzene, 1,4-bis(mercaptomethyl)benzene, 2,2'-dimercaptobiphenyl, 4,4'-dimercaptobiphenyl, bis(4-mercaptophenyl)methane, 2,2-bis(4-mercaptophenyl)propane, bis(4-mercaptophenyl)ether, bis(4-mercaptophenyl)sulfide, bis(4-mercaptophenyl)sulfone, bis(4-mercaptomethylphenyl)methane, 2,2-bis(4-mercaptomethylphenyl)propane, bis(4-mercaptomethylphenyl)ether, bis(4-mercaptomethylphenyl)sulfide, 2,5-dimercapto-1,3,4-thiadiazole, 3,4-thiophenedithiol, 1,1,3,3-tetrakis(mercaptomethylthio)propane, 1,2,6,7-tetramercapto-4-thiaheptane, and pentaerythrithiol.

* * * * *